United States Patent [19]

Hortig et al.

[11] 3,977,091

[45] Aug. 31, 1976

[54] TEMPERING AND STERILIZING DEVICE

[75] Inventors: Hans-Peter Hortig, Frankfurt am Main; Hans Pfeiffer, Bad Soden, Taunus, both of Germany

[73] Assignee: Hoechst Aktiengesellschaft, Frankfurt am Main, Germany

[22] Filed: May 24, 1972

[21] Appl. No.: 256,366

Related U.S. Application Data

[63] Continuation-in-part of Ser. No. 53,234, July 8, 1970, abandoned.

[30] Foreign Application Priority Data

July 19, 1969 Germany.............................. 1936865

[52] U.S. Cl.................................... 34/105; 34/34; 34/225; 34/233; 165/120; 21/78
[51] Int. Cl.²........................................ F26B 25/00
[58] Field of Search................. 165/120, 107; 34/34, 34/54, 105, 225, 233; 55/DIG. 29; 21/78, 79, 80; 426/408; 98/33, 40 D

[56] References Cited
UNITED STATES PATENTS

| | | | |
|---|---|---|---|
| 3,252,400 | 5/1966 | Madl, Jr................... | 55/DIG. 29 |
| 3,303,771 | 2/1967 | Nesher et al.............. | 55/DIG. 29 |
| 3,367,257 | 2/1968 | Raider et al............. | 98/33 |
| 3,418,915 | 12/1968 | Marble................... | 55/DIG. 29 |
| 3,505,989 | 4/1970 | Truhan................... | 55/DIG. 29 |
| 3,574,952 | 4/1971 | Lee, Jr................... | 34/105 |
| 3,711,957 | 1/1973 | Carver, Jr................ | 34/34 X |

FOREIGN PATENTS OR APPLICATIONS 526,346   9/1940   United Kingdom................. 34/225

*Primary Examiner*—Albert W. Davis, Jr.
*Attorney, Agent, or Firm*—Curtis, Morris & Safford

[57] ABSTRACT

A device for tempering and/or sterilizing objects which must be kept free of contamination by foreign particles, such as for example, ampules sterilized in pharmaceutical preparations, has a housing and means for supporting the objects in the housing. A pair of gas distribution plates are mounted in the housing in spaced relationship to each other, on either side of the support means, and cooperate with means for supplying conditioned air to produce a laminar flow of the conditioned air downwardly over the objects being treated. The conditioned air has a substantially different temperature than the objects being treated and can be either heated or cooled depending upon whether the device is used for sterilizing or tempering. Because of the maintenance of laminar flow in the housing, the number of contaminating particles per space unit which can come into contact with the objects being treated is decreased.

20 Claims, 2 Drawing Figures

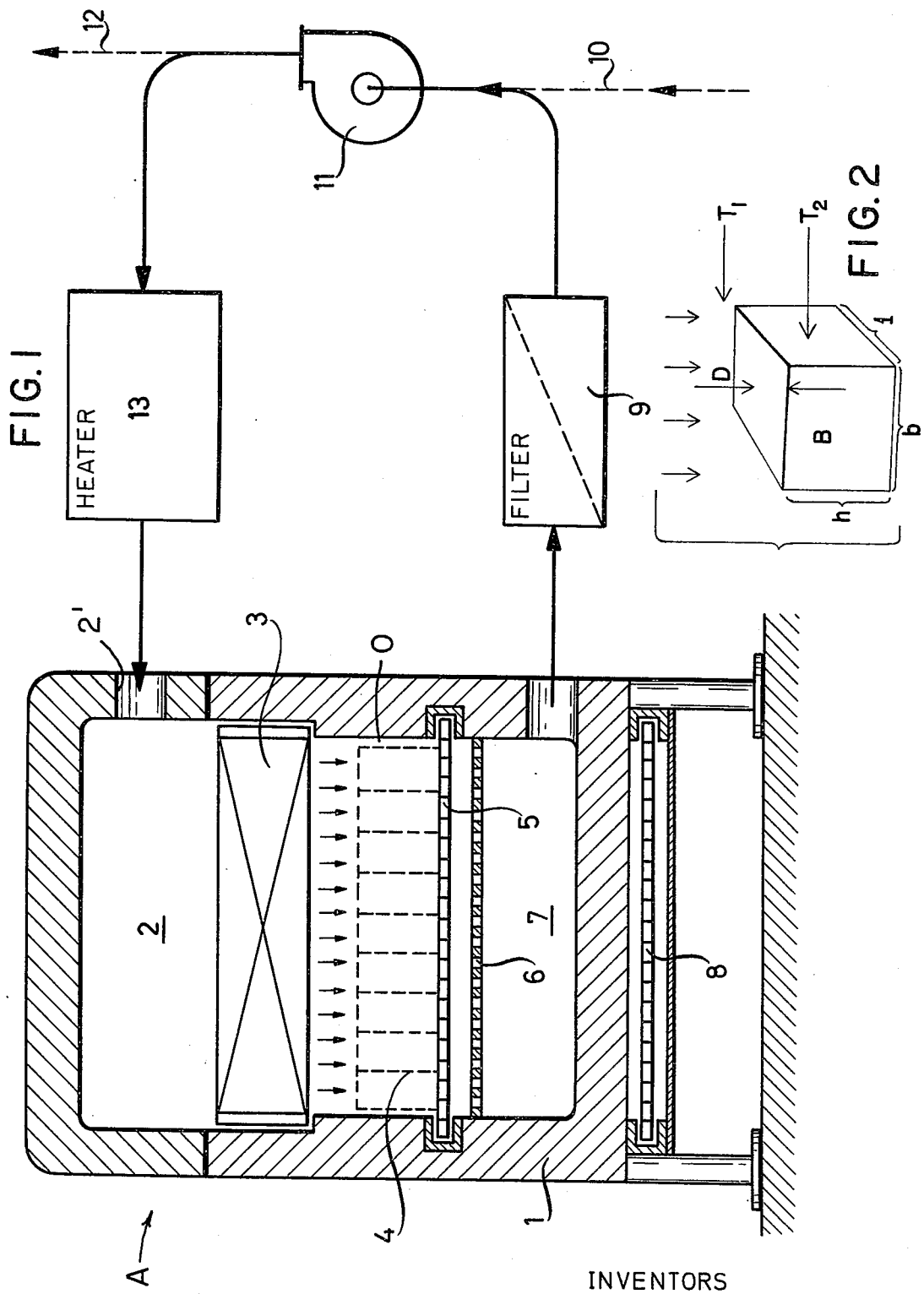

TEMPERING AND STERILIZING DEVICE

This application is a continuation-in-part of copending U.S. patent application Ser. No. 53,234, filed July 8, 1970, the disclosure of which is incorporated herein by reference.

The present invention relates to tempering and/or sterilizing apparatus and more particularly to a tempering and/or sterilizing apparatus having the shape of an enclosed cabinet or tunnel for receiving and heating or cooling objects to be treated.

Apparatus of the above type is typically utilized as a cooling furnace for tempering hot glass ampules or as sterilizing cabinets or tunnels in packaging plants for sterile packaging of ampules and the like to be used with pharmecutical preparations. A number of tempering and sterilizing devices have previously been proposed which are constructed as discontinuously operated cabinet units or as continuously operated tunnel units. For discontinuous operation the cabinet units are provided, for example, with hurdles upon which the objects being treated are supported. On the other hand, for continuous operation, tunnel type units are provided with conveying means, for example, open mesh grab chains or conveyor belts, for transporting the objects through the tunnel. In such previously proposed systems heating is generally effected by means of radiators, while cooling is accomplished with the help of a gas stream flowing through the device.

While other such systems are used as sterilizing units, or tempering units, it has been found that uncontrollable convection currents are produced within the previously proposed devices because of the heat supplied by the radiators during sterilization or by the heat of the objects being cooled during tempering. As a result, abrading particles accompanying the objects being treated, which are unavoidably obtained during the manufacture of the ampules and during their placement in the treatment cabinet or tunnel, are distributed over the interior of the device and in the objects being treated.

In such previously proposed sterilizing devices, up to 10,000 particles per liter of air of greater than 0.5 micron dimension, have been counted; while in tempering units, where cooling air flow is supplied to hot ampules or objects, the measured values of undesirable particles are sometimes even higher. As a result of this unavoidable contamination of goods to be treated in previously proposed sterilizing and tempering units, there exists a relatively high reject rate for objects treated thereby. A typical reject rate for such sterilizing devices is approximately 7% which, with a production rate of approximately 20,000 ampules per hour, means that 1,400 ampules per hour are non-usable. Further, with previously proposed tempering devices, the objects being treated must be subsequently purified or sterilized thoroughly in order to eliminate the objectionable contamination particles placed on them during the cooling process.

Heretofore, it has not been possible to reduce the number of particles in the interior of the device so that the disadvantageous contamination of objects being treated could be eliminated. Accordingly, such contamination had to be tolerated or eliminated by subsequent treatment.

In accordance with the present invention the contamination of objects in tempering and sterilizing devices is substantially reduced in a closed cabinet or tunnel in which the tempering or sterilizing process is performed by utilizing a conditioned air flow supplying heating or cooling air, depending on the desired operation of the device, which air is passed through the device in a laminar flow so that it first strikes the objects being treated and then passes through the support for the objects.

While the use of laminar flow is known in many applications (c.f. for example I. M. Pilcher, Ingenieur Digest 9, (1968), 71/75) and is known particularly for use in clean rooms wherein objects are manufactured, such as for example, aircraft and spacecraft guidance systems, the use of such laminar flow has not heretofore been applied to tempering and sterilizing devices. This is because it has heretofore been believed in the art that laminar flow is limited by the temperature gradient within the clean room or enclosure in which it is produced. In this regard, reference is had to a paper published by D. Regensheit in Chemi-Ingenieur-Technik, Volume 41, NR 19, 1969, Pages 1050–1056 (and in particular page 1052). This paper, in general, relates to laminar flow considerations in air containing constructions and, on page 1052 thereof, it is indicated that with a chamber of approximately 3 meters in height, the temperature differential between incoming and outgoing air due to heat produced within the chamber should only be about 0.3°C in order to maintain laminar flow conditions. The article also points out that in conventional production chambers or rooms, it is normally to be expected that the change in temperature across the room between the incoming and outgoing air will be from 1° to 10° C per meter. With such high temperature gradients, the air exchange in the room, in order to maintain laminar flow, must be between 100 to 300 air changes per hour. That is, the total air volume in the room must be changed 100 to 300 times per hour. Accordingly, that article indicates that with relatively high temperature differences, such as occur in the tempering and sterilizing devices with which the present invention is concerned, it would not be expected that laminar flow could be maintained, because convection currents resulting from the high temperature gradients in the chamber, would prevent the maintenance of laminar flow.

Similarly, U.S. Federal Standard 209(a), published by the General Services Administration under the Federal Property and Administrative Service Act of 1949, and in particular, paragraph 30.2 thereof, indicates that the temperature differences in clean rooms or chambers in which laminar flow is to be maintained should not exceed ± 5°F (2.8°C). At temperature differences within the room or chamber above this temperature, the air flow in the room becomes turbulent, destroying the laminar flow.

Applicants have found, on the other hand, that by the construction of the present invention, as described herein, it is possible to maintain laminar flow conditions in a tempering and/or sterilizing device wherein vast temperature gradients are maintained. For example, in the sterilizing mode of operation of the device of the present invention the ampules supplied to the chamber are at a predetermined temperature, e.g. ambient temperature, with heated air supplied to the chamber at approximately 300°C greater than the temperature of the ampules themselves. On the other hand, in the tempering mode of operation, the ampules are supplied to the device after manufacture and have a temperature of approximately 350°C while cooling air is supplied thereto through the device at approximately 50°C in order temper and cool the ampules. From the above mentioned articles and the Federal Standard, it would appear that because of the vast temperature gradient within the chamber during operation of the device, in either the tempering or sterilizing modes, it would not be possible to maintain laminar flow conditions. However, by the construction of the invention applicants have obtained these conditions even with such vast temperature gradients and has achieved great advantages over the prior art. In fact, it has been found that with the construction of the invention, utilizing laminar flow in a sterilization chamber, the rate of rejects of ampules being treated is reduced from the 7% reject rate for the prior art apparatus to approximately 0.1% for that of the present invention. Thus, with a normal production rate of 20,000 ampules per hour, only 20 or less ampules are rejected with the laminar flow structure of the present invention. Accordingly, there is a substantial increase in the usable throughput of sterilizing devices constructed in accordance with the present invention.

These advantages of the invention are achieved because the number of foreign particles and the disturbance thereof in the interior of the device is considerably reduced as compared with previously proposed devices. Moreover, the laminar flow enables the transport or supply of heat to be calculated more exactly and consequently the device can be dimensioned more safely. Further, when the apparatus of the invention is charged with wet objects to be treated, liquid vapors can escape in a reliable manner, because of the laminar flow, so that damage to the structure due to corrosion is substantially avoided. The laminar flow also prevents hot and cold gases from being mixed with one another in neighboring zones, thereby avoiding turbulence within the structure and eliminating the need for specialized compartmentalization. Owing to the heat or conditioned air supply in a laminar flow, the objects being treated are in fact treated under milder conditions and compartmentalization with respect to series connected objects is relatively simple.

The above and other features and advantages of this invention will be apparent in the following detailed description of an illustrative embodiment thereof which is to be read in connection with the accompanying drawings, wherein:

FIG. 1 is a diagrammatic illustration of a tempering and sterilizing device constructed in accordance with one embodiment of the present invention; and FIG. 2 is a diagrammatic illustration of a predetermined volume of air utilized to describe the features of the invention.

Referring now to the drawing in detail and initially to FIG. 1 thereof, it is seen that a tempering and/or sterilizing device A, constructed in accordance with the present invention, includes a sterilizing tunnel or cabinet 1 defining a distribution channel or chamber 2 for the conditioned air or gas which is to be supplied to the tunnel. Before entering the work space 4, containing the goods to be sterilized, the conditioned air supplied to distribution channel 2, through an opening 2' therein, passes through a distributing device or plate 3.

In the illustrative embodiment of the invention, distributing device 3 may comprise a main filter for the air being supplied to the objects being treated in the work space. It is also possible, however, to use a separate main filter outside of the tempering or sterilizing device, for example, in the air flow line leading into connection 2'. In this case distributing device 3 constitutes a simple distribution plate provided with a plurality of fine apertures or slots which define a predetermined pressure loss in the work space 4 therebelow in order to produce the required laminar flow. In a preferred embodiment of the invention the distribution plate can be provided with apertures having a diameter of 0.2 to 0.6 mm., with the total area of the passage formed by the apertures defining a maximum of 10% of the area of the plate. Preferably, this area is limited to 3–5%.

Air supplied to chamber 4 flows therethrough in a laminar flow pattern between the objects 0 supported in the work space. These objects can be supported on a perforated conveyor 5, which may constitute simply a perforated belt or an open chain, grip-type conveyor in which the objects 0 are seated. Alternatively, if housing 1 is a cabinet rather than a flow through tunnel, support means 5 can be a fixed plate having a plurality of apertures therethrough.

In any case, the apertures in support 5 permit the laminar flow of air supplied through the distribution plate 3 to pass therethrough towards a second distribution plate 6. This plate is provided with a plurality of apertures in the same manner as plate 3 and serves to cooperate with plate 3 to maintain laminar flow within work space 4 and to assure a uniform distribution of the gases into a collecting chamber 7 defined within cabinet 1 below plate 6. Further, distribution plate 6 also cooperates with plate 3 to maintain the desired pressure within the work space to insure laminar flow.

In the illustrative embodiment of the invention support means 5 is an endless conveyor whose upper flight or reach extends through the work space 4 to support the objects being treated. The return reach 8 extends below the housing outside of work space 4, as illustrated in the drawing.

From collection chamber 7 the air is returned through a primary filter 9 by a blower or pump 11. Blower 11 may be supplied with fresh air as desired to supplement the returned air, through a fresh air line 10 having appropriate valve control means as would occur to those skilled in the art. From the blower the air from the return line and the fresh air which has been added, if any, is returned to the tempering or sterilizing device through a gas heater 13 which serves to heat or condition the air to the desired temperature for the tempering or sterilizing operation. In addition, if desired, a portion of the gas from blower 11 may be removed as waste through line 12.

In a typical operation of the invention during the sterilizing process, ampules or the like are supplied to cabinet 1 at a predetermined temperature, which generally is approximately equal to the ambient temperature. In this case heater 13 is operated to raise the temperature of the air supplied to the cabinet to a sufficient temperature at which the ampules will be sterilized. This temperature typically will be approximately 300°C higher than the temperature of the ampules being supplied. On the other hand, when the device is used for tempering heated ampules, the ampules are supplied at a temperature of approximately 350°C and the temperature of the air supplied from heater 13 to distribution chamber 2 is approximately 50°C, so that again the temperature difference is 300°C.

In one embodiment of the invention cabinet 1 has a total height of approximately 1 meter or less, with the distance between the distribution plates 3 and 6 being between 0.5 meters and 0.3 meters.

By this construction of the invention, laminar flow is at all times maintained within work space 4 during the tempering and sterilizing operations. As mentioned above, the fact that laminar flow is thus, in fact, maintained, is totally unexpected in view of the knowledge of artisans skilled in the art prior to this invention. In fact, it can be shown mathematically that it would be expected that laminar flow would not be maintained within the construction of the invention with such vast temperature gradients within the work space 4.

This can be shown by referring to FIG. 2 of the drawing. That figure illustrates a volume of air having a unit volume defined as $b \times l \times h$ upon which the dynamic pressure D of the air currents supplying the air and the buoyancy B of the unit volume of air itself are acting. This buoyancy is the result of the temperature of the air in the predetermined volume due to the temperature conditions contained within the work space. It is clear that laminar flow in the volume of air will be maintained as long as the dynamic force D is greater than the buoyancy force B so as to prevent turbulent air flow. As soon as the buoyant force becomes greater than the dynamic force, laminar flow is interrupted and turbulence occurs because of the convection currents.

Consider now FIG. 2 with respect to the operation of the device when operated in its tempering mode. In this case the temperature of air coming into the device and applying the dynamic pressure D is represented as $T_1$, while the temperature of the volume of air being acted upon is $T_2$, i.e. the temperature of the air at the ampules to be cooled. In the preferred embodiment of the invention $T_1$ equals 50°C (or 323°K) while $T_2$ is 350°C (or 623°K). In addition, the air is typically supplied at a velocity equal to 0.3 meters per second.

The dynamic pressure applied to the air volume illustrated in FIG. 2 can be represented by the equation:

$$D = \frac{\gamma_1}{2g} v^2 bl \qquad 1.$$

where $g = 9.81$ m/sec.$^2$ and $\gamma_1$ = the specific gravity of the air entering the chamber.

Similarly, the buoyancy of the volume of air illustrated in FIG. 2 can be represented by the equation:

$$B = blh (\gamma_1 - \gamma_2) \qquad 2.$$

where $\gamma_2$ = the specific gravity of the volume of air being acted upon.

By combining equations (1) and (2) for the limiting condition of laminar flow, where B = D, that is, the condition at which laminar flow will terminate, as described above, the following equation is obtained:

$$\frac{\gamma_1}{2g} v^2 = h(\gamma_1 - \gamma_2) \qquad 3.$$

This equation can be reduced according to the laws of ideal gases, and to the relationship of the densities of the gases to their absolute temperatures, so that the following equation results, giving the temperature difference which must occur for laminar flow to be maintained:

$$T_2 - T_1 = \frac{v^2 T_2}{2gh} \qquad 4.$$

Inserting into equation (4) the known variables described above, i.e. gas velocity v equals 0.3 meters/sec.; the height of the tunnel h equals 0.3 m.; and the temperature of the entering ampules $T_2 = 623°K$; it appears that:

$$T_2 - T_1 = \frac{0.09 \times 623}{2 \times 9.81 \times 0.3} = 9.5°K. \qquad 5.$$

Thus, by the above equations it is shown that theoretically the maximum permissible temperature difference should be 9.5°C, instead of about 300°C, in order to maintain laminar flow conditions within the chamber illustrated in FIG. 1. However, it has been found that in that operation, laminar flow conditions are maintained throughout the device even with the temperature gradient of approximately 300°C between the actual temperature of the ampules being treated and the conditioned air being supplied to the work space.

Accordingly, it is seen that even though the prior knowledge in the field, as indicated by the above calculations and the previously discussed references, would indicate to one skilled in the art that it would not be possible to maintain laminar flow conditions under the operating conditions utilized within the construction of the present invention, it has in fact been found that with the described construction laminar flow conditions can be maintained with such high temperature gradients. These conditions are maintained even with a continuously operated system wherein the conveyor 5, 8 is continuously moved. In addition, discontinuously operated devices, in accordance with the invention, such as for example, closed cabinets, operate with laminar flow conditions in the same manner.

Although an illustrative embodiment of the present invention has been described herein with reference to the accompanying drawing, it is to be understood that the invention is not limited to that precise embodiment and that various changes and modifications may be effected therein by one skilled in the art without departing from the scope or spirit of this invention.

What is claimed is:

1. A device for tempering objects which are to be kept free from contamination by foreign particles which comprises, a housing, means for supporting said objects in said housing, a first gas distribution plate mounted in said housing above said supporting means and having a plurality of relatively small apertures therein, a second gas distribution plate mounted in said housing, below and in spaced relation to said supporting means and having a plurality of relatively small apertures therein, said first and second plates cooperating to define a work space in said housing about the objects to be treated on said supporting means, means for supplying conditioned air to said housing at the side of said first plate remote from said supporting means at sufficient pressure for said conditioned air to flow into said work space, said conditioned air having a substantially different temperature than said objects, and said first and second plates providing a predetermined pressure drop between their opposite faces to produce a laminar flow of conditioned air downwardly from said first plate over the objects on said supporting means through said supporting means and second plate for discharge from said housing; said supporting means having a plurality of openings therein to permit said laminar flow therethrough; said objects having a temperature of approximately 350°C. and said conditioned air being supplied at approximately 50°C. to temper and cool said objects.

2. The device as defined in claim 1 wherein said supporting means comprises a perforated conveyor for transporting said objects through said work space in the housing.

3. The device as defined in claim 1 wherein said means for supplying conditioned air supplies air to said housing at a velocity of approximately 0.3 m/sec.

4. The device as defined in claim 1 wherein the vertical distance between said first and second plates is between 0.5 m and 0.3 m.

5. The device as defined in claim 4 wherein the apertures in said distribution plate have diameters between 0.2 mm and 0.6 mm and wherein said apertures define a maximum of 10% of the total areas of their respective plates.

6. The device as defined in claim 1 wherein said conveyor means comprises an endless conveyor having an upper reach for transporting objects through said work space and a lower reach outside of said work space and housing.

7. The device as defined in claim 6 wherein said first distribution plate comprises a main filter for the conditioned air supplied to said work area.

8. The device as defined in claim 7 wherein said means for supplying conditioned air includes a return line connected between said housing and said blower for returning air passing through said second distribution plate to said blower.

9. The device as defined in claim 8 wherein said return line includes a preliminary filter for said return air.

10. The device as defined in claim 1 wherein said first distribution plate cooperates with said housing to define a distribution chamber on the side of said plate remote from said conveyor, said means for supplying conditioned air to said housing being connected to supply air to said chamber for even distribution over said first plate, prior to passage therethrough.

11. A device for sterilizing objects which are to be kept free from contamination by foreign particles which comprises, a housing, means for supporting said objects in said housing, a first gas distribution plate mounted in said housing above said supporting means and having a plurality of relatively small apertures therein, a second gas distribution plate mounted in said housing, below and in spaced relation to said supporting means and having a plurality of relatively small apertures therein, said first and second plates cooperating to define a work space in said housing about the objects to be treated on said supporting means, means for supplying conditioned air to said housing at the side of said first plate remote from said supporting means at sufficient pressure for said conditioned air to flow into said work space, said conditioned air having a substantially different temperature than said objects, and said first and second plates providing a predetermined pressure drop between their opposite faces to produce a laminar flow of conditioned air downwardly from said first plate over the objects on said supporting means through said supporting means and second plate for discharge from said housing; said supporting means having a plurality of openings therein to permit said laminar flow therethrough; said objects being supplied to said housing at a predetermined temperature and said means for supplying conditioned air supplying said air at a temperature approximately 300°C. greater than said predetermined temperature to sterilize said objects.

12. The device as defined in claim 11 wherein said means for supplying conditioned air supplies air to said housing at a velocity of approximately 0.3 m/sec.

13. The device as defined in claim 11 wherein the vertical distance between said first and second plates is between 0.5 m and 0.3 m.

14. The device as defined in claim 13 wherein the apertures in said distribution plate have diameters between 0.2mm and 0.6mm and wherein said apertures define a maximum of 10% of the total areas of their respective plates.

15. The device as defined in claim 11 wherein said conveyor means comprises an endless conveyor having an upper reach for transporting objects through said work space and a lower return reach outside of said work space and housing.

16. The device as defined in claim 15 wherein said first distribution plate comprises a main filter for the conditioned air supplied to said work area.

17. The device as defined in claim 16 wherein said means for supplying conditioned air includes a return line connected between said housing and said blower for returning air passing through said second distribution plate to said blower.

18. The device as defined in claim 12 wherein said return line includes a preliminary filter for said return air.

19. The device as defined in claim 11 wherein said first distribution plate cooperates with said housing to define a distribution chamber on the side of said plate remote from said conveyor, said means for supplying conditioned air to said housing being connected to supply air to said chamber for even distribution over said first plate, prior to passage therethrough.

20. The device as defined in claim 11 wherein said supporting means comprises a perforated conveyor for transporting said objects through said work space in the housing.

* * * * *